(12) United States Patent
Twisselmann (10) Patent No.: US 6,471,165 B2
(45) Date of Patent: Oct. 29, 2002

(54) SURGICAL MICROSCOPE AND STAND ASSEMBLY

(75) Inventor: Lorenz Twisselmann, Prisdorf (DE)

(73) Assignee: Moller-Wedel GmbH, Wedel (DE)

( * ) Notice: Subject to any disclaimer, the term of this patent is extended or adjusted under 35 U.S.C. 154(b) by 0 days.

(21) Appl. No.: 09/841,338

(22) Filed: Apr. 24, 2001

(65) Prior Publication Data

US 2002/0014562 A1 Feb. 7, 2002

(30) Foreign Application Priority Data

Apr. 25, 2000 (EP) .............................................. 00108786

(51) Int. Cl.⁷ .............................................. F16M 13/00
(52) U.S. Cl. .............................. 248/123.11; 248/280.11; 248/281.11; 248/278.1; 248/125.7; 248/585; 901/8; 901/9; 359/382; 359/384
(58) Field of Search ......................... 248/122.1, 123.11, 248/125.7, 125.9, 282.1, 280.11, 281.11, 284.1, 278.1, 585; 901/8, 9, 24, 41, 44, 47; 359/362, 368, 382, 384

(56) References Cited

U.S. PATENT DOCUMENTS

| | | | |
|---|---|---|---|
| 4,548,373 A | * 10/1985 | Komura | ...................... 188/171 |
| 4,881,709 A | * 11/1989 | Nakamura | ............. 248/123.11 |
| 5,213,293 A | 5/1993 | Muentener et al. | .... 248/123.11 |
| 5,273,039 A | 12/1993 | Fujiwara et al. | ............ 600/407 |
| 5,332,181 A | 7/1994 | Schweizer et al. | ..... 248/123.11 |
| 5,609,316 A | * 3/1997 | Tivliev | ................... 248/123.11 |
| 6,364,268 B1 | * 4/2002 | Metelski | ................... 248/278.1 |

FOREIGN PATENT DOCUMENTS

| | | |
|---|---|---|
| DE | 43 20 443 A | 12/1994 |
| DE | 43 34 069 A | 4/1995 |
| DE | 197 32 212 A | 1/1999 |
| EP | 0023003 | * 7/1980 |
| EP | 0023004 | * 7/1980 |
| EP | 0 552 524 A | 7/1993 |
| EP | 0 849 053 A | 6/1998 |

* cited by examiner

Primary Examiner—Leslie A. Bruan
Assistant Examiner—Deborah M. Brann
(74) Attorney, Agent, or Firm—Alix, Yale & Ristas, LLP (57) ABSTRACT

The surgical microscope with a stand, the microscope having altogether up to six degrees of freedom and being fixed on the microscope mounting by means of elements of the stand which has two vertical pivoting axes and for the height adjustment a parallelogram linkage with weight compensation is distinguished by the fact that the microscope is mounted on the stand by means of a third vertical axis, a first further axis perpendicular to said third vertical axis and a second further axis perpendicular to the first further axis, the further axes being designed such that they are essentially perpendicular to the optical axis of the microscope objective and can be adjusted by motor, and the further axis that is closer to the microscope permitting a lateral pivoting of the viewing direction and the further axis that is arranged between the third vertical axis and the further axis that is closer to the microscope permitting a pivoting of the viewing direction forward/backward or upward/downward.

20 Claims, 10 Drawing Sheets

SURGICAL MICROSCOPE AND STAND ASSEMBLY

BACKGROUND OF THE INVENTION

The invention relate to a surgical microscope with a stand, the microscope having altogether up to six degrees of freedom and being fixed on the microscope mounting by means of elements of the stand, the stand having two vertical pivoting axes, which are not subjected to any gravitational influence, and for the height adjustment a parallelogram linkage with weight compensation, which are formed in such a way that they can move smoothly and have arresting brakes.

In the case of such a stand (U.S. Pat. No. 5,213,293), the microscope can be brought into the desired position for the surgery with the aid of the stand. It has a weight compensation, so that it remains in this position even when articulating joints undergo slight braking. However, it is very laborious to accomplish this weight compensation. Subsequent adjustment of the microscope to change the image field must be performed manually.

In the case of another known microscope (U.S. Pat. No. 5,232,181), the adjustment about all the axes takes place in a motorized manner. For this purpose, only approximate weight compensation is required, which of course, is easier to accomplish than the fine compensation of the first-mentioned arrangement. The problem of this arrangement is that the setting of the microscope to a new assignment or new conditions by the motors takes place only very slowly, since fast automatic movements about the individual degrees of freedom would require motors that are too large and, in particular, are also dangerous. This nullifies the advantage that only approximate balancing is required.

For the manual handling of a surgical microscope on a stand, balancing is always required. It is not only weight compensation by counterweight, springs and pneumatic springs that is necessary, since the arms of the stand are of a certain weight, which is of course always the same. When adjustments are made to accessories of the microscope, which become necessary when performing operations, the center of gravity of the microscope shifts. Renewed weight compensation about the rotational axes then has to be performed. Taking into consideration the necessary rigidity of the microscope mounting, the mechanical complexity when there are a plurality of axes of rotation is considerable and, if it is wished to make weight compensation easier for the user, is further increased by motor drives. There are even known configurations (German Patent Nos. DE 4320443 A and DE 43 34 069 A) in which the weight compensation is carried out automatically on request by sensors, controllers and actuating elements.

SUMMARY OF THE INVENTION

The object of the invention is to provide a microscope with a stand with which the setting of the location of the microscope can be quickly performed manually, but a fine setting of the observable image field can be subsequently performed, without this handling being disturbed by gravitational forces or moments caused as a result of the latter.

Briefly stated, the invention in a preferred form involves the microscope being mounted on the stand by means of a third vertical axis, which is not subject to any gravitational influence. A first further axis is perpendicular to said third vertical axis and a second further axis is perpendicular to the first further axis. The further axes are designed such that they are essentially perpendicular to the optical axis of the microscope objective and can be adjusted by motor. The further axis that is closer to the microscope permits a lateral pivoting of the viewing direction (X direction) and the further axis that is arranged between the third vertical axis and the further axis that is closer to the microscope permits a pivoting of the viewing direction forward/backward or upward/downward (Y direction).

It is indeed known to free the mobility of surgical microscopes on supporting units by buttons on grips which are arranged on the microscope. When the buttons are actuated, electromotive brakes of the articulating joints of the stand are released. However, the invention is not confined to the capability of being able to perform the movements about these axes quickly by hand and then block the axes in this position. Rather, the invention also provides a combination of this manual adjusting capability with a motorized setting.

The relatively great adjusting distances of the stand are made available to the user/surgeon in a way known per se and a weight-compensated manner in the so-called "free floating mode." The user guides the device by a grip, for example with an integrated button, by which the movement can be enabled. At the same time, a fine weight compensation has been performed at the parallelogram arm. This overall weight compensation must be as accurate as possible, so that only very small forces are required for the settings. An imbalance at the two setting axes directly on the microscope does not present any problem if a motorized adjustment is provided for these axes and the motors are powerful enough to absorb the corresponding forces of the imbalance.

The rotations about the third vertical axis and the two further axes allow the surgeon to adapt the field of view to requirements. The special sequence of the two further axes at the same time provides a very expedient adjustability for different surgery conditions. This is because the optical axis of the surgical microscope is aligned completely differently in relation to the vertical for different surgical operations (for example, brain operations, spinal operations, and eye operations). If the sequence of the further axis is chosen to be different, this favorable alteration of the field of view is no longer possible.

The motor drives are expediently designed as servo drives. The set point input for these servo functions is performed in a preferred way by electrical force or moment sensors between the microscope and the operating element for the corresponding directions. The sensors are designed in such a way that they emit a signal which rises with the moment exerted by the user and occurring at the operating element about an axis and changes its algebraic sign when there is a change in direction. The operating elements are expediently adjustable, so that the user can adjust them into the position most comfortable for the user, without at the same time changing the position of the sensors in relation to the microscope, and consequently, the relationship between the signals and the effective direction.

In the case of longitudinal and transverse forces and in the case of moments perpendicular to the sensor axis, no signal is emitted. In a particularly expedient embodiment, the sensors are arranged in pairs in such a way that, when one sensor is relieved by a force exerted on the operating element by an operator, the other sensor is loaded. The two sensors are arranged on either side of a neutral line with respect to the moment to be detected or the force to be detected. The two sensors are under a pressure and are connected to each other in a bridge circuit, so that the signals produced by the pressure cancel each other out. If a moment or a force attempting to bring about a rotation about this line is introduced into the operating element, rising pressure occurs on one side of the neutral line, falling pressure on the other side. In a corresponding way, the bridge is unbalanced and supplies an output signal corresponding to the moment. Piezo elements, inductive sensors, capacitive pickups, resistive and optical force/displacement pickups may be used as sensors.

The signals are further processed in terms of control technology to perform the adjustments by means of motor drivers and servomotors. With adequate dynamics of the two servo controllers together with the free floating of the other four degrees of freedom, the setting times are reduced. While the user adjusts the microscope in the four degrees of freedom freed for movement, the moments introduced for setting the direction of the microscope axis act at the same time on the operating element and bring about the corresponding adjustment of the microscope with relatively great displacements and the servo adjustment of the small rotational movements does away with the effect known from purely servo systems that the user has to wait for a long time until the adjustment is completed.

The arrangement is expediently set up in such a way that the possible movements about the individual axes or degrees of freedom are limited to such an extent that the microscope cannot hit parts of the stand.

BRIEF DESCRIPTION OF THE DRAWINGS

The invention is described below on the basis of advantageous embodiments with reference to the attached drawings, in which.

DETAILED DESCRIPTION OF THE PREFERRED EMBODIMENT

Figure 1:
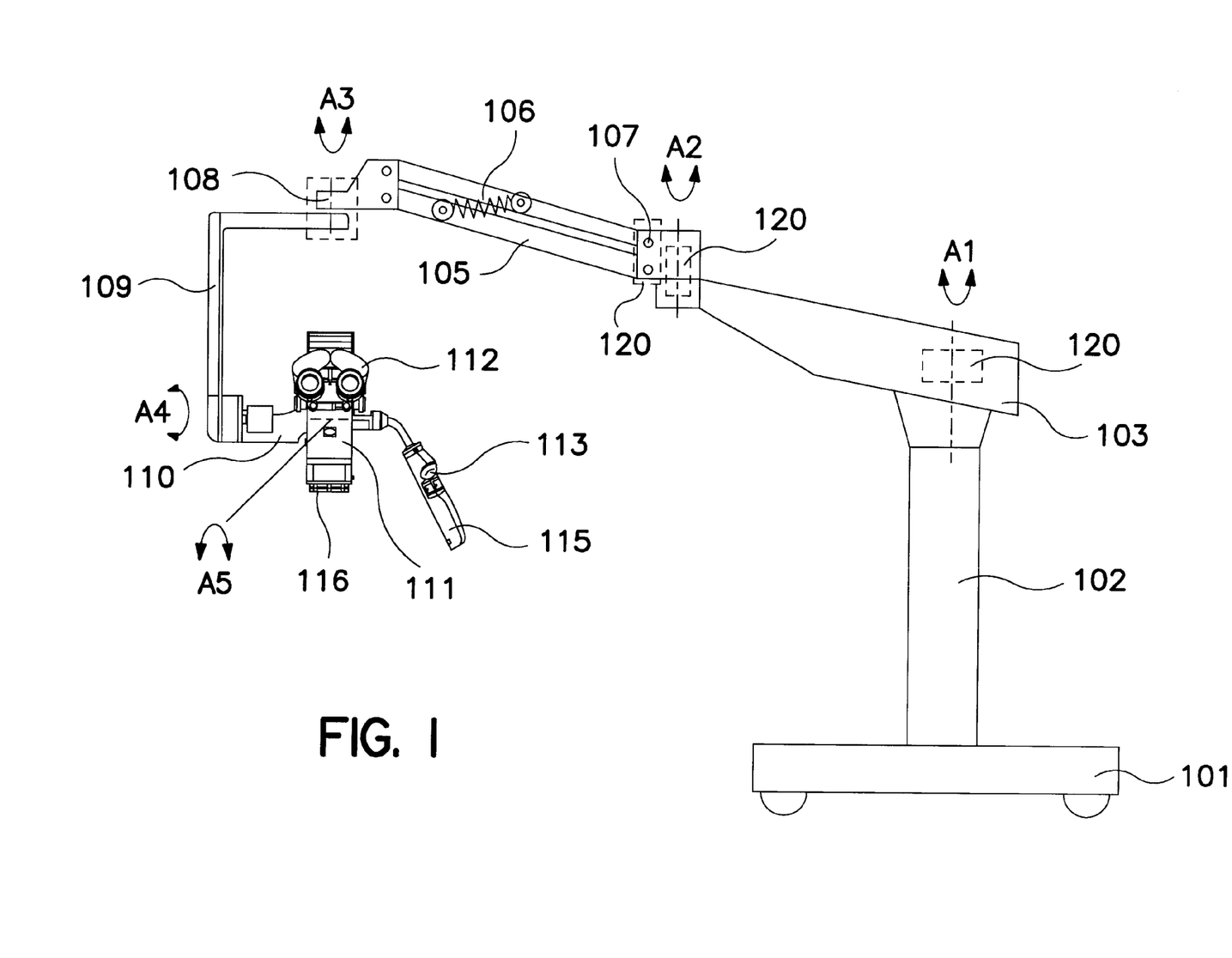
FIG. 1 shows the basic construction of the stand according to the invention in a side view.

Represented in FIG. 1 is the arrangement of a surgical microscope on a floor stand. The stand is standing on a base part or foot 101, which is generally provided with rollers for travel. It goes without saying that the base part 101 may also be designed for affixing to a ceiling or a wall. Attached on this base part 101 is a column 102, about the axis A1 of which the mounted fixed arm 103 can rotate. With an articulating joint that can rotate about the axis A2, a parallelogram arm 105 is fixed to said arm. The height adjustment of the microscope connection 108 on the parallelogram 105 is weight-compensated by a pneumatic spring or a spring assembly 106.

The microscope comprises a microscope body 111, an eyepiece 112 and an objective 116 and is fixed by arms 110 and 109 to the microscope connection of the stand in such a way that it can rotate about the axis A3. It can be moved by the rotations about the axes A1, A2 and A3 and by the weight-compensated height adjustment with the parallelogram arm 105 in the mechanically predetermined space free from gravitational influence, restricted only by frictional resistances.

Figure 2:
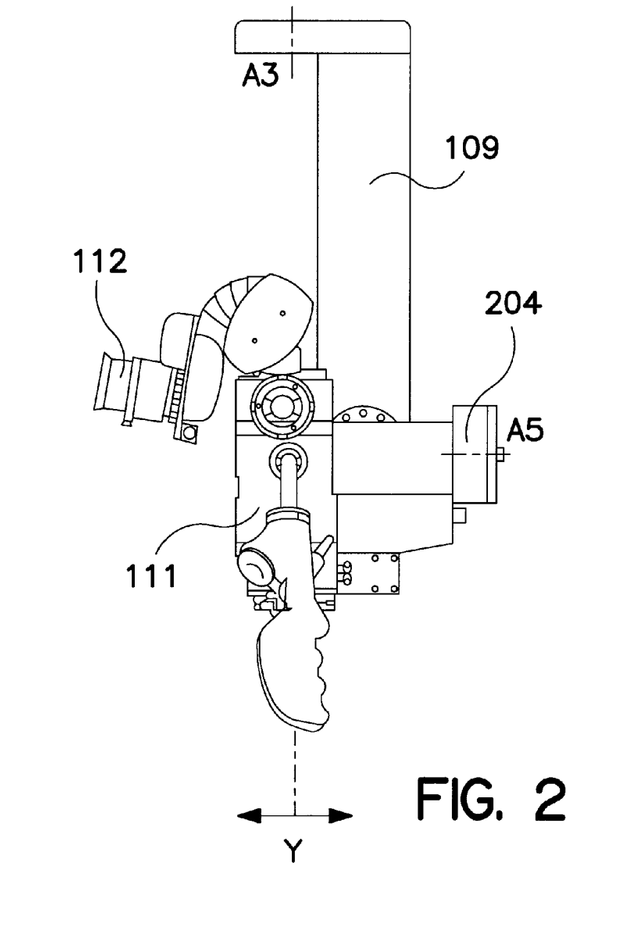
FIG. 2 shows the microscope in side view.
Figure 3:
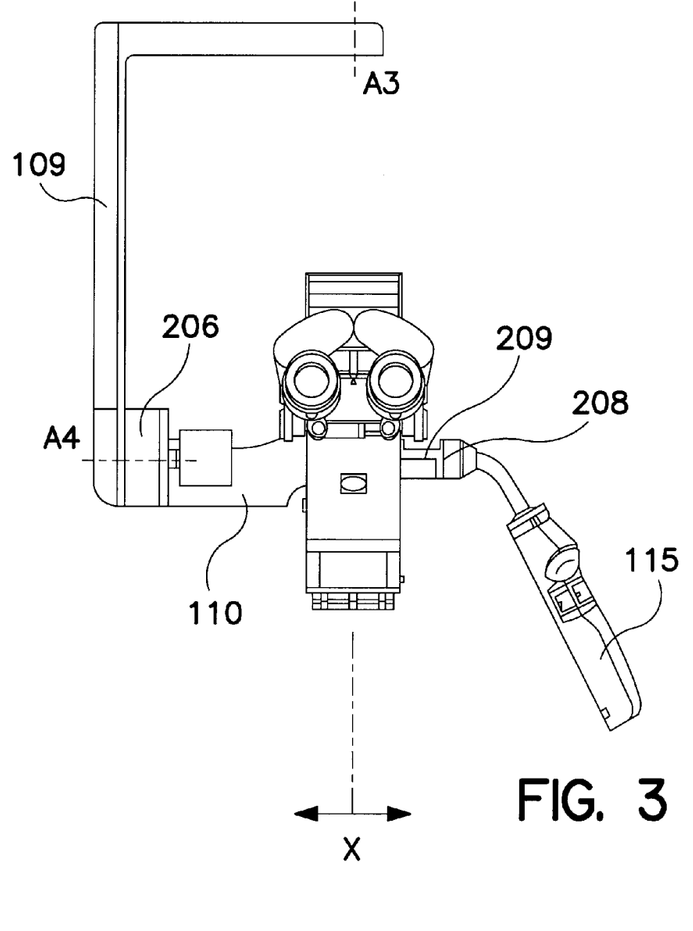
FIG. 3 shows the microscope in a front view.

As presented in FIGS. 1–3, the microscope 111 represented there can be rotated by the servo drive 204 about the axis A5. This corresponds to a rotation in the field of view in the lateral direction (X direction). Together with the arm 110, the microscope 111 can be rotated by the servo drive 206 about the axis A4. This corresponds to a movement in the field of view upward/downward (Y direction).

Figure 4:
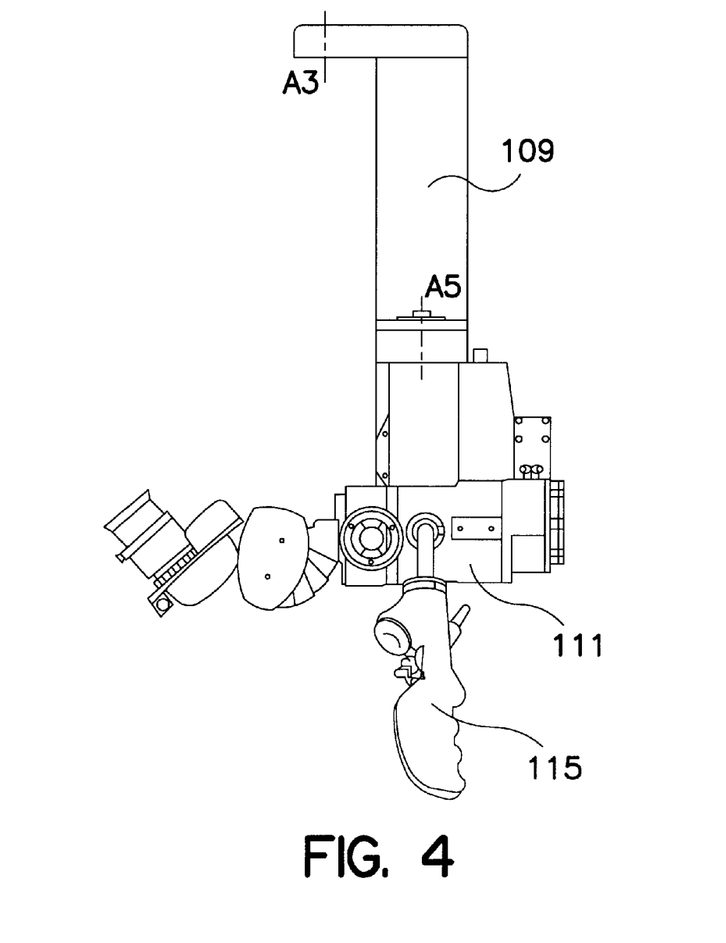
FIG. 4 shows the microscope in a similar representation to that in FIG. 2 after it has been rotated 90°.
Figure 5:
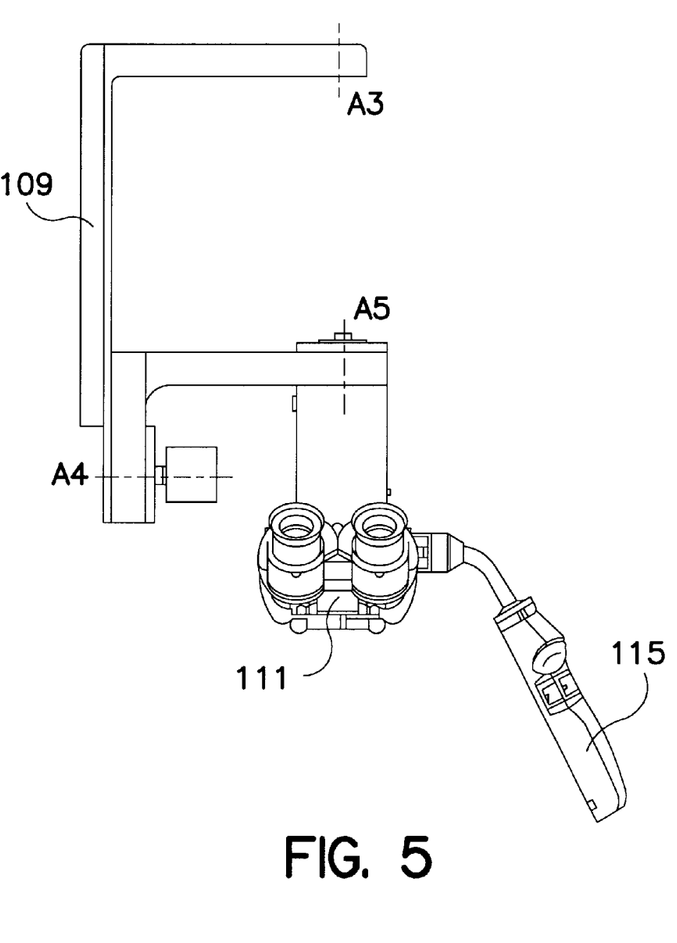
FIG. 5 shows the microscope in a similar representation to that in FIG. 3 after it has been rotated 90°.

In FIGS. 4 and 5, the arrangement is shown in a similar representation to that in FIGS. 2 and 3, although the microscope 111 has been rotated 90° about the axis A4, so that the axis of the objective is horizontal.

Figure 6:
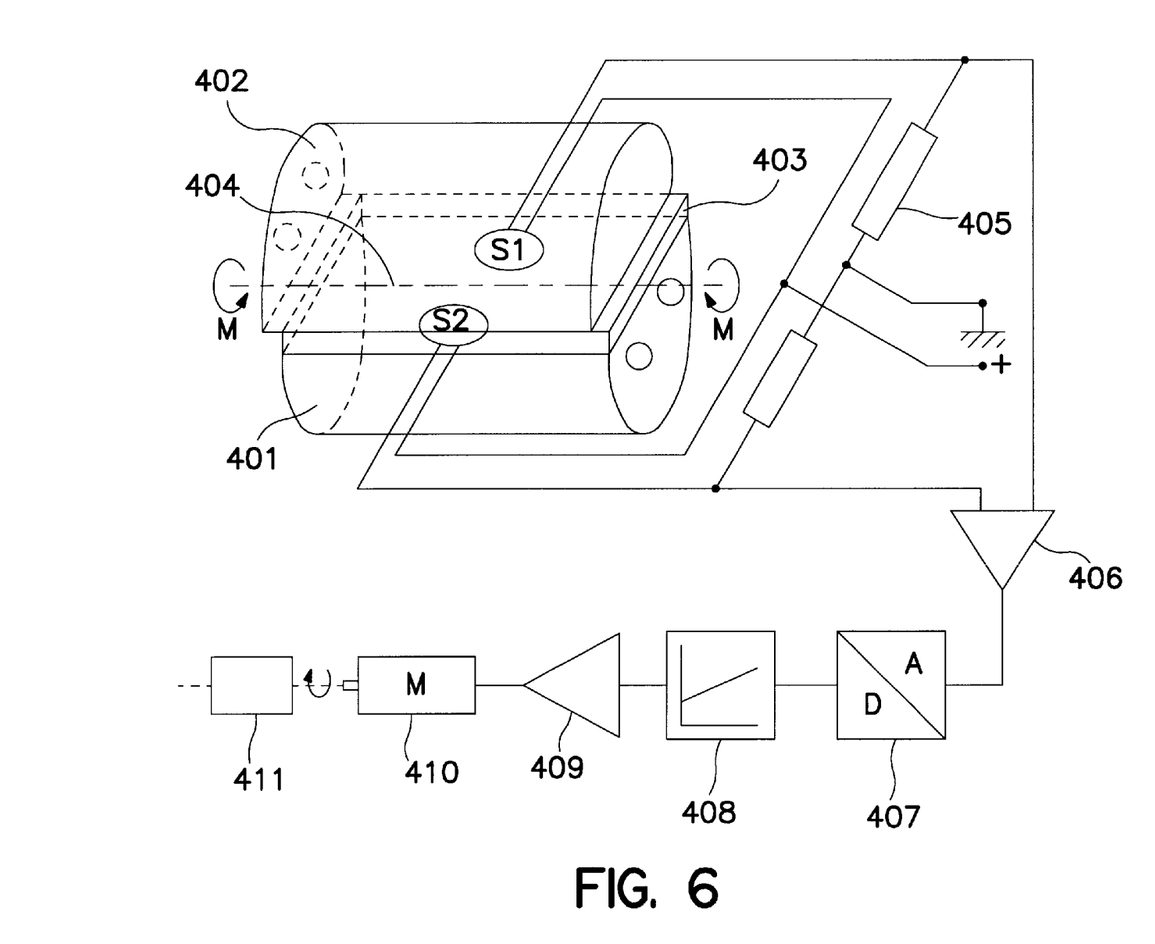
FIG. 6 shows the basic construction of the sensors and electrical evaluation circuits.

In FIG. 6, a force and moment sensor for the Y adjustment is represented schematically and by way of example. A flexible sheet 403 is stretched between the bodies 401 and 402. Arranged in it are two pressure sensors S1 and S2. If a moment M acts between the two bodies 401 and 402, amplified and attenuated compressive forces are produced in the flexible sheet 403 on the two sides of a neutral phase 404 and induce changes in resistance in the sensors S1 and S2. The further processing of the signals takes place with the bridge circuit 405, the amplifier 406, the analog/digital converter 407, control-technological processing 408 and a driver 409 for the stepping motor 410 for the servo adjustment of the axis A4.

As mentioned, the movement about the axes A1, A2 and A3 and that of the parallelogram linkage 105 is smooth, so that an adjustment can be easily performed. The arresting then takes place by means of the brakes 120, which are indicated in FIG. 1 by dashed lines. These brakes can be released for the approximate adjustment, by the corresponding button 113 on the operating element 115 being actuated. The drive of the motors can act directly on the corresponding axes. However, it is also possible to interpose a gear mechanism, which is indicated in FIG. 6 at 411.

Figure 7:
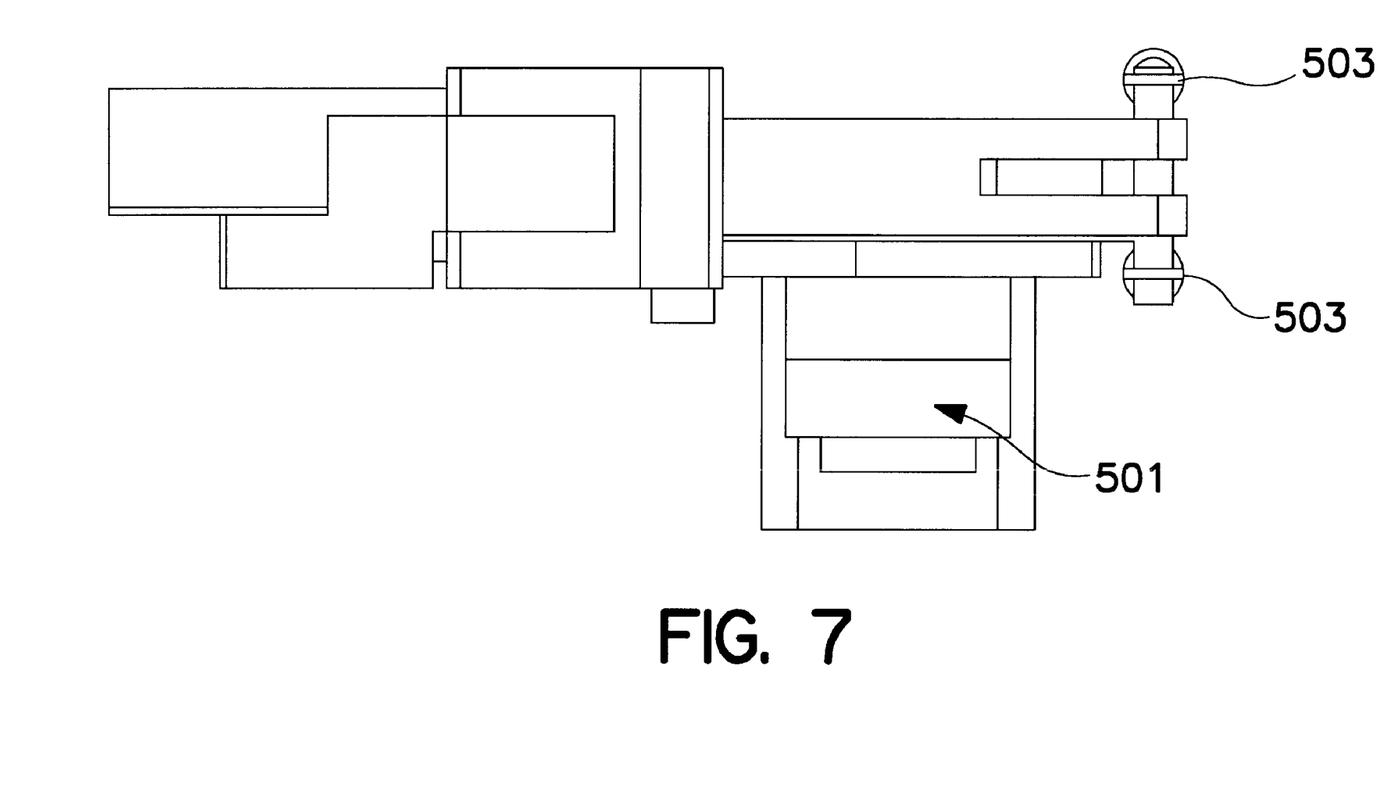
FIG. 7 shows an enlarged side view of a brake mechanism for the microscope.
Figure 8:
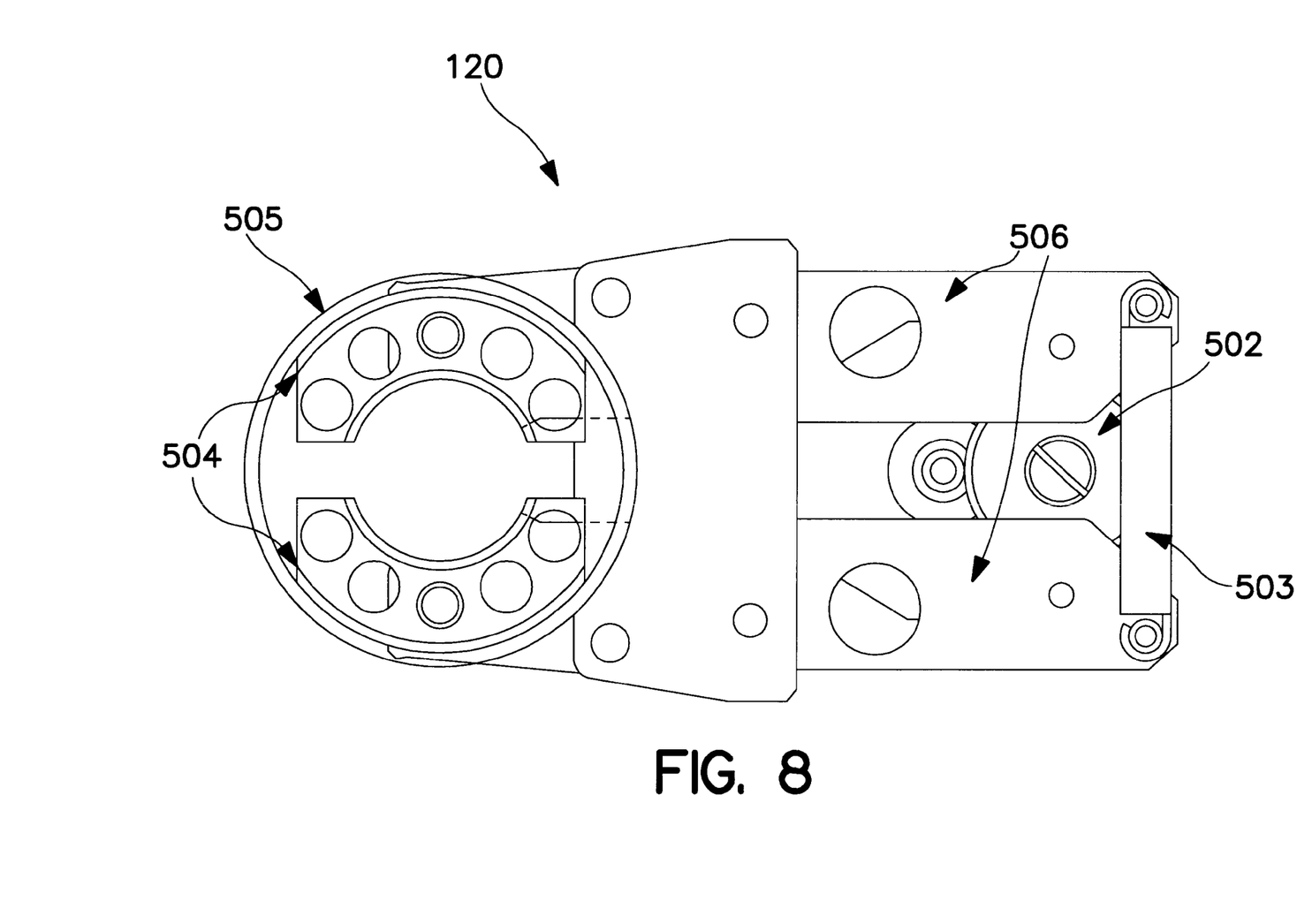
FIG. 8 shows an interior generally top view of the brake mechanism of FIG. 7.

With reference to FIGS. 7 and 8, the pivot axes A1 and A2 are provided with disk brakes 120. Two springs 503 via levers 506 urge brake shoes 504 against a rotating drum 505. In order to release the brakes, the brake levers 506 are pressed away from each other by the elliptical body 502 which is actuated by step motor 501 so that the brake shoes 504 are released from the brake drum 505. In the current-free condition, the brake is activated or reset by the tension spring 503. The electric power supplied to the step motor 501 for actuating and releasing the brakes is switched on and off with a button via electric cables. Such cables are also provided for the power supply from an electric energy source (e.g., 110 or 220 V). the cables in the vicinity of the microscope are arranged outside of the device. They extend through the parallelogram linkage 105 and through a hollow axis of pivot axis A2 to the main circuit board (not illustrated).

Figure 9:
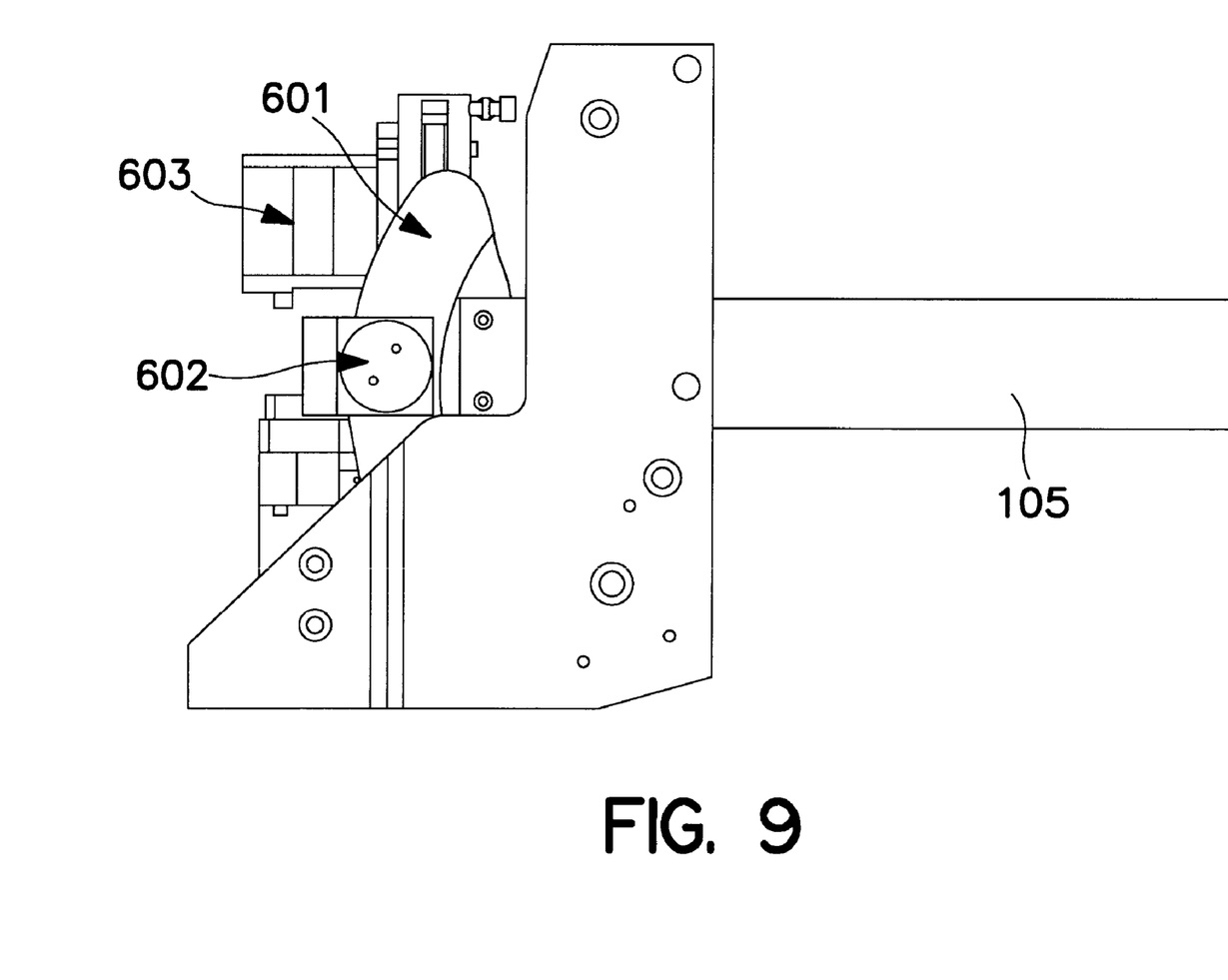
FIG. 9 shows an enlarged broken way view of a second brake mechanism for the microscope.
Figure 10:
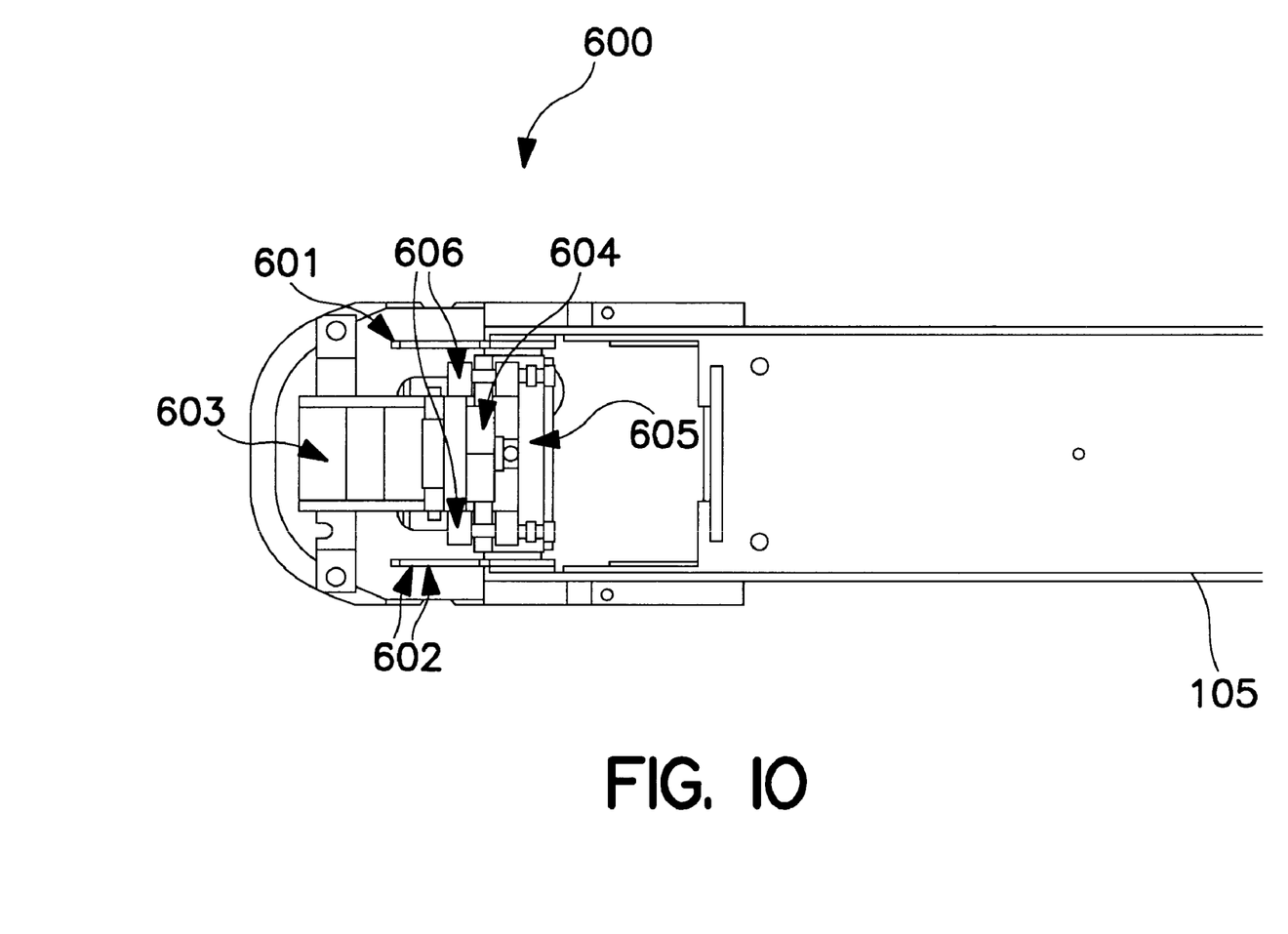
FIG. 10 shows a broken way enlarged top view generally of a brake mechanism of FIG. 9.

Not only pivot axes A1 and A2 are provided with brakes 120, but also brakes are provided for the parallelogram linkage 105. For this purpose a disk brake 600 is employed (see FIGS. 9 and 10). A disk segment 601 is fixed to a parallelogram arm 105. It is clamped or pinched between two brake shoes 602. Tension spring 605 presses the brake shoes 602 via two levers 606 against the disk segment. Step motor 603 urges levers 606 apart from each other via an elliptical disk 604 to release the brake. In the current-free condition tension spring 605 pulls levers 606 together and presses the brake shoes 602 against the disk segment.

Figure 11A:
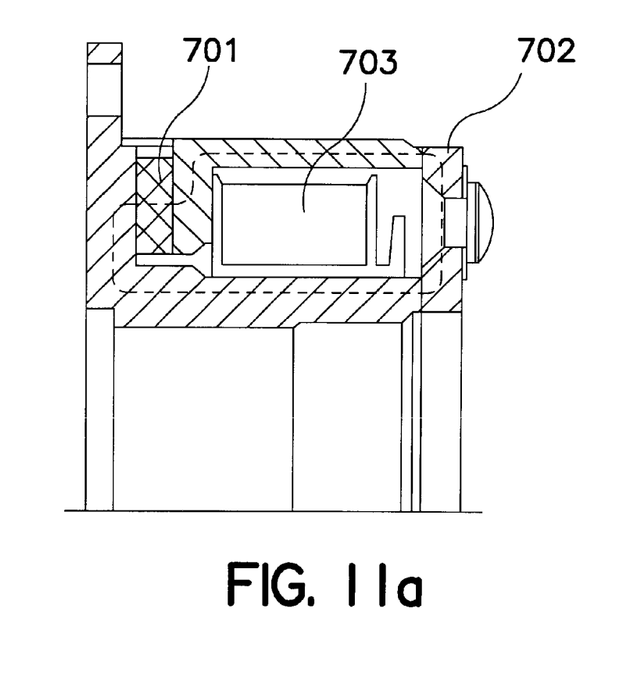
FIGS. 11a and 11b are generally sectional views, each showing a third brake mechanism employed in the microscope showing respective breakdown on brake positions.
Figure 11B:
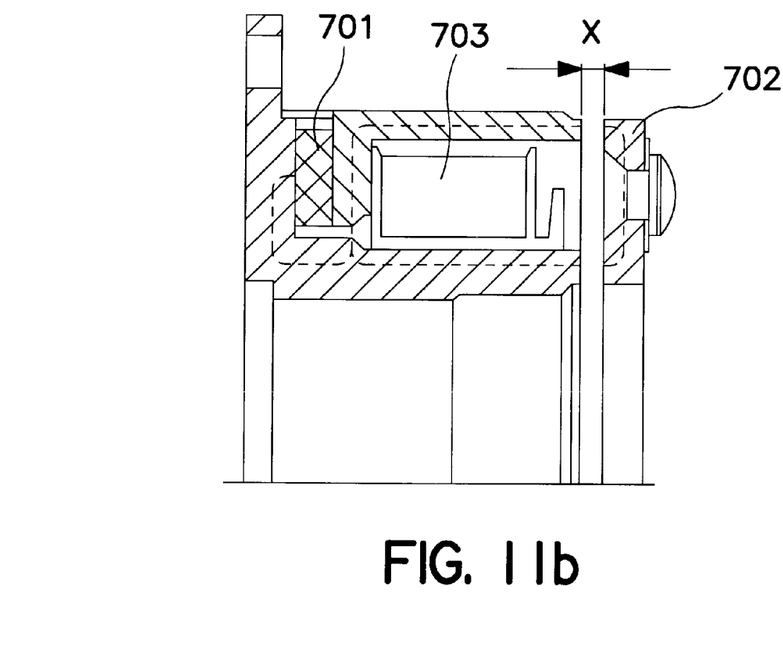

Also pivot axis A3 is provided with a magnetic brake (FIGS. 11a and 11b). Under current-free conditions permanent magnet 701 attracts a brake disk 702 against a braking surface of the magnet and therefore acts in a braking manner on the rotation. As the electromagnet 703 energized by electric current, a repulsive force acts on brake disk 702 which is moved away from the braking surface of the magnet as shown in FIG. 11b. The braking action is no longer present. One form of a COMBIPERM brake, available from KEB Antriebstechnik of Germany.

Figure 12:
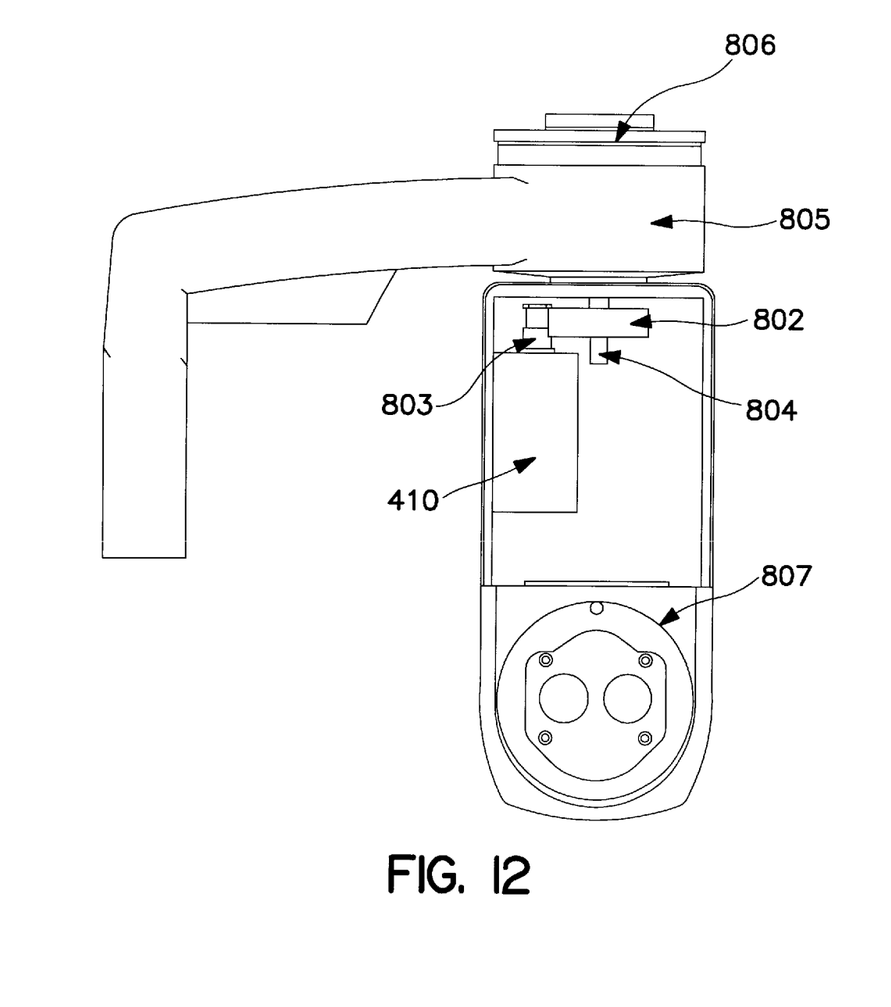
FIG. 12 is an enlarged view partly broken away showing a motor and drive train mechanism employed in the microscope.

For the drive a brushless DC servo motor Type 3056 B of the Company Faulhaber of Germany is used. The motor drivably connects the drive (FIG. 12) via two toothed pulleys 802 and 803 (number of teeth: 48 and 10, respectively) and a cog belt on a gear 806 (Harmonic Drive Getriebeeinbausatz HFUC-14-2UH of the company Harmonic Drive Antriebstechnik GmbH of Germany) via axis 804. The driving end of gear 806 is fixed to the support 805. The power takeoff side of gear 806 is connected to the microscope body 807 such that the microscope body 807 is rotated with a ratio of 1:480 with respect to the rotation of the motor axis. The gear ratios for gear mechanism 411 are as follows:

| | |
|---|---|
| Reduction ratio by Harmonic Drive | 1:100 |
| Reduction ratio by belt drive | 1:4.8 |
| Total reduction rate | 1:480 |

There is a similar mechanism for axis A5. The pivotal adjustments relative to both axes A4 and A5 are adjusted by two independently controlled motors 410.

What is claimed is:

1. A surgical microscope/stand assembly comprising:
   a microscope comprising an objective defining an optical axis; and
   a stand comprising:
   a base positionable to define a generally horizontal reference plane including an X and Y axis; and
   a movable linkage assembly connecting said base and said microscope and comprising:
   a support mounted to said base;
   a first arm pivotally mounted to said support for pivoting about an axis A1;
   a parallelogram linkage assembly mounted to said first arm for pivotal movement about an axis A2, said linkage assembly being vertically positionable relative to said base and comprising weight compensation means and brake means for selectively fixing the position of the linkage assembly;
   a second arm mounted to said linkage for pivotal movement about an axis A3;
   a third arm mounted to said second arm for pivotal movement about an axis A4, said axis A4 being substantially perpendicular to the third axis A3;
   a first motor drive for adjusting the pivotal position of said third arm about axis A4;
   said microscope mounted to said third arm for pivotal movement about an axis A5, said axis A5 being substantially perpendicular to said axis A4; and
   a second motor drive for adjusting the pivotal position about axis A5,
   wherein axes A1, A2 and A3 are substantially vertical, and said axes A4 and A5 are substantially perpendicular to the optical axis, and the pivoting about said axis A5 permitting lateral pivoting of the X viewing direction and the pivoting about said axis A4 permitting pivoting of the Y viewing direction.

2. The assembly as claimed in claim 1, wherein at least one motor drive is a servo drive.

3. The assembly as claimed in claim 2, and further comprising at least one operating element and two sensors for controlling a servo drive are arranged between the microscope and at least one operating element and generate signals corresponding to the size and direction of a force or torque exerted on at least one operating element, for the appropriate control of a motor of the said motor drive.

4. The assembly as claimed in claim 3, wherein at least one operating element is adjustable, without changing the position of the sensors in relation to the microscope.

5. The assembly as claimed in claim 3, wherein the sensors are arranged in a pair in such a way that, when one sensor is relieved by a force exerted on the operating element by an operator, the other sensor is loaded.

6. The assembly as claimed in claim 5, wherein the sensors are arranged in a bridge circuit which emits a voltage determining the direction and speed of the motorized adjustment.

7. The assembly as claimed in claim 6, further comprising a circuit for converting the voltage into a supply voltage for a servo drive.

8. The assembly as claimed in claim 6, further comprising a stepping motor for a servo drive, an analog/digital converter for the voltage and signal circuit for output signals of the analog/digital converter for generating activation signals for the stepping motor.

9. The assembly as claimed in claim 1, wherein the drives each have a gear mechanism.

10. The assembly as claimed in claim 1, wherein the possible movements about the individual axes are limited.

11. The assembly as claimed in claim 3, wherein the sensors have optical pickups with small displacements.

12. The assembly as claimed in claim 3, wherein the sensors have capacitive pickups.

13. The assembly as claimed in claim 3, wherein the sensors have inductive pickups with small displacements.

14. The assembly as claimed in claim 3, wherein the sensors have piezo elements.

15. The assembly as claimed in claim 1, further comprising a magnetic brake for selectively fixing the pivotal position about axis A3.

16. The assembly as claimed in claim 15, further comprising an electromagnet engaged to release the brake.

17. The assembly as claimed in claim 1, further comprising a brake for selectively fixing the pivotal position about axis A1.

18. The assembly as claimed in claim 17, further comprising a stepping motor for releasing the brake.

19. The assembly as claimed in claim 1, further comprising a brake for selectively fixing the pivotal position about axis A2.

20. The assembly as claimed in claim 19 further comprising a stepping motor which activates to overcome a spring force to release the brake.

* * * * *